United States Patent
Backhaus et al.

(10) Patent No.: US 8,482,853 B2
(45) Date of Patent: Jul. 9, 2013

(54) STEREO MICROSCOPE SYSTEM

(75) Inventors: Christoph Backhaus, Weitnau/Wengen (DE); Holger Matz, Unterschneidheim (DE)

(73) Assignee: Carl Zeiss Meditec AG, Jena (DE)

( * ) Notice: Subject to any disclaimer, the term of this patent is extended or adjusted under 35 U.S.C. 154(b) by 665 days.

(21) Appl. No.: 12/694,530

(22) Filed: Jan. 27, 2010

(65) Prior Publication Data
US 2010/0188740 A1    Jul. 29, 2010

(30) Foreign Application Priority Data
Jan. 28, 2009    (DE) .......................... 10 2009 006 407

(51) Int. Cl.
*G02B 21/06*    (2006.01)
(52) U.S. Cl.
USPC ......................................... 359/388; 359/376
(58) Field of Classification Search
USPC ................................. 359/388, 376
See application file for complete search history.

(56) References Cited

U.S. PATENT DOCUMENTS

| | | | |
|---|---|---|---|
| 5,838,491 A * | 11/1998 | Gartner et al. | 359/385 |
| 7,206,128 B2 * | 4/2007 | Tonooka | 359/388 |
| 2002/0018292 A1 | 2/2002 | Koetke | |
| 2005/0207004 A1 * | 9/2005 | Tokunaga et al. | 359/383 |

FOREIGN PATENT DOCUMENTS

| | | |
|---|---|---|
| DE | 1 938 835 B1 | 9/1971 |
| DE | 103 36 476 B4 | 6/2007 |
| EP | 1 109 046 A1 | 6/2001 |

* cited by examiner

*Primary Examiner* — Alessandro Amari
(74) *Attorney, Agent, or Firm* — Potomac Patent Group, PLLC

(57) ABSTRACT

An illumination system of a microscopy system comprises an actuator configured to change an angle of an illumination light beam and a mirror assembly, which is selectively positionable into the beam path of the illumination light beam. The mirror assembly may comprise an actuator configured to change an orientation of a mirror with respect to another mirror.

21 Claims, 4 Drawing Sheets

STEREO MICROSCOPE SYSTEM

CROSS-REFERENCES TO RELATED APPLICATIONS

The present application claims priority to German Patent Application No. 10 2009 006 407.9, filed Jan. 28, 2009, entitled "Stereo Microscope System," the contents of which is hereby incorporated by reference in its entirety.

BACKGROUND OF THE INVENTION

The invention relates to a stereo microscope system having an illumination system configured to illuminate an object to observe by the microscope system.

A stereo microscope system can be used by a surgeon in a surgical procedure to provide a magnified image of a field of operation. Herein, a conventional stereo microscope system comprises microscope optics for imaging an object which can be located in an object plane of the microscope optics and an illumination system for directing an illumination light beam towards the object plane.

In some situations there is a problem in performing a surgical procedure in a body cavity which has a small entrance aperture. The imaging beam path of the microscope optics has to extend through this entrance aperture, and the illumination light has to traverse the entrance aperture to enter into the body cavity. It has been found that conventional systems are insufficient in directing a desired amount of illumination light into the body cavity.

SUMMARY OF THE INVENTION

The present invention has been accomplished taking the above problems into consideration.

It is an object of the present invention to provide a stereo microscope system having an illumination system which can be adapted to various illumination requirements.

According to embodiments of the invention, a microscope system having an illumination system can be used to illuminate deep and narrow body cavities.

Further embodiments of the invention provide a stereo microscope system comprising microscope optics configured to image an object, the microscope optics having an object plane and including an objective lens having an optical axis, and an illumination system configured to direct a first illumination light beam towards the object plane, wherein a central axis of the first illumination light beam is oblique with respect to an optical axis of the objective lens. The illumination system further comprises a mirror assembly, which is displaceable by an actuator between a first state and a second state, the mirror assembly being positioned in a beam path of the first illumination light beam in the first state and being removed from the beam path of the first illumination light beam in the second state. When the mirror assembly is removed from the beam path of the first illumination light beam, the first illumination light beam can impinge onto the object plane, wherein the orientation of the central axis of the first illumination light beam is oblique with respect to the optical axis of the objective lens. When the mirror assembly is positioned in the beam path of the first illumination light beam, the first illumination light beam is deflected consecutively by at least two mirrors of the mirror assembly such that the first illumination light beam impinges also onto the object plane, wherein, however, the angle between the central axis and the optical axis of the objective lens is smaller than in the second state, in which the mirror assembly is not positioned in the beam path.

According to exemplary embodiments, the illumination system comprises an actuator configured to change an angle between the central axis of the first illumination light beam and the optical axis.

According to a further exemplary embodiment, the illumination system comprises an actuator configured to change an orientation of the first mirror or of the second mirror or of both mirrors of the illumination system relative to the central axis of the first illumination light beam.

According to a further exemplary embodiment, the stereo microscope system comprises an actuator configured to displace lenses of the objective lens with respect to each other in order to change a distance between the object plane and the objective lens. The distance between the object plane and the objective lens is also referred to as a working distance of the stereo microscope system.

It is not necessary to include all of the actuators mentioned above in combination in one embodiment. Each of these actuators can be used alone or in combination with one or more of the other actuators in the stereo microscope system. Each of these actuators can comprise a drive, such as a motor, controlled by a controller of the microscope system. It is, however, also possible that the actuators are driven by hand rather than automatically by a motor under automatic control of the controller of the microscope system. For example, the actuators can be driven by a hand-driven adjusting screw or a hand-driven slider, wherein such actuator can also be implemented by being hinged mechanically to one of the other actuators and being adjustable together with this one.

According to further embodiments of the invention, each one of the two mirrors can have a planar reflective surface, a concave reflective surface or a convex reflective surface.

BRIEF DESCRIPTION OF THE DRAWINGS

In the following description, the present invention is explained in more detail with respect to exemplary embodiments and in relation to the accompanying drawings, in which.

DETAILED DESCRIPTION OF THE INVENTION

Figure 1:
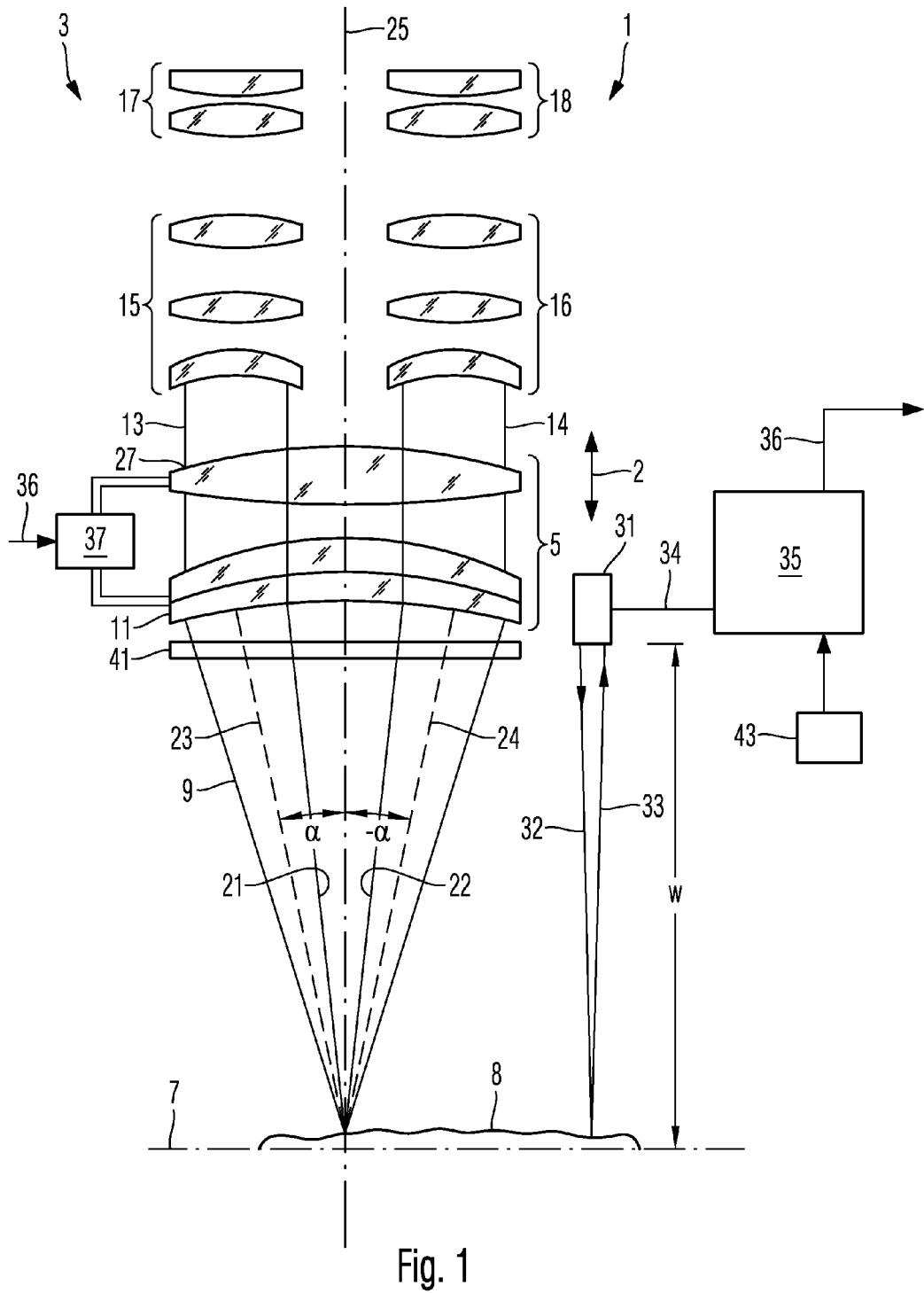
FIG. 1 is a schematic illustration of components of a stereo microscope system.

In the following, a configuration and a function of a stereo microscope system will be explained with respect to FIG. 1 which is a schematic illustration showing other components of the stereo microscope system. As shown in FIG. 1, the stereo microscope system 1 comprises microscope optics 3 having an objective lens 5, wherein an object under examination which is to be imaged by the microscope optics 3 can be disposed in an object plane 7 of the objective lens 5. Light emanating from the object plane 7 as a conical beam bundle 9 enters a front lens 11 of the objective lens 5 and is transformed into an image side beam bundle by the objective lens 5. A portion of the light of the image side beam bundle enters into zoom optics 15 as a left observation beam bundle 13, traverses zoom optics 15 and generates an image of the object plane 7 in an ocular 17, into which a user of the microscope system 1 can look with his left eye. Similarly, a further portion of the light of the image side beam bundle enters into zoom optics 16 as a right observation beam bundle 14, traverses the zoom optics 16 and generates a further image of the object plane 7 in an ocular 18, into which the user can look with his right eye.

The light emanating from the object plane 7 and contributing to the generation of the image in the left ocular 17 is a partial beam bundle denoted with reference numeral 21 in FIG. 1, wherein a central axis 23 of the partial beam bundle 23 is oriented under an angle a with respect to an optical axis 25 of the objective lens 5. Similarly, the light contributing to the image of the object plane 7 in the right ocular 18 is a partial beam bundle of the beam bundle 9 denoted with reference numeral 22 in FIG. 1, wherein a central axis 24 of the partial beam bundle 22 is oriented under an angle −a with respect to the optical axis 25. As both partial beam bundles 21, 22 emanate from the object plane 7 under different angles for generating the image in the left ocular 17 and the right ocular 18, respectively, the images generated in the oculars 17, 18 are perceived as stereoscopic images by the user of the microscope system 1.

In the illustrated embodiment, the objective lens 5, comprises two lens assemblies comprising a front lens 11 of the microscope optics 3 and a further lens 27 which can be displaced in a direction parallel to the optical axis 25 with respect to the front lens 11, as indicated schematically by an arrow 29 in FIG. 1. The displacement of the two lens assemblies 11 and 27 with respect to each other causes a change in a working distance w between the front lens 11 and the object plane 7. Such change of the working distance w of the microscope optics 3 may become necessary, if the object under examination is moved closer to the front lens 11 or farther away from it.

In the schematic illustration of FIG. 1, optical lenses are shown in a simplified representation. In practice, however, a lens shown in a simplified representation in FIG. 1, may comprise one or more lens elements which are disposed at a distance from each other or may be in contact with each other to form a cemented lens group.

In the illustrated example, the stereo microscope system 1 comprises a front plate 41 which is disposed in front of the objective lens 5 to protect the same. The front plate 41 has two parallel planar surfaces and does not have an optical power, such as a focusing or defocusing optical power.

In the example shown in FIG. 1, the stereo microscope system 1 comprises a distance sensor 31 configured to emit measuring radiation 32 towards the object 7 and to receive measuring radiation 33 reflected by the object 7 so as to measure a working distance w. A detection signal of the distance sensor 31 is transmitted to a controller 35 via a data line 34. The controller 35 controls an actuator 37 in dependence on the detection signal via a control line 36.

The actuator 37 is configured to displace the lens 27 of the objective lens 5 relative to the lens 11 for adjusting the object plane 7 such that the object plane 7 approximately coincides with the surface of the object 8 for generating images of the surface of the object 8 in the oculars 17, 18.

The actuator 37 controlled by the controller 35 may comprise a motor, such as an electric motor generating a rotation or a piezo electric motor generating a translation. In order to actuate optical components, the actuator is mechanically coupled to optical components by, for example, a lever, a register, a slider, a carriage or the like. It is, however, also possible that the user actuates the actuator 37 by hand rather than the actuator 37 being controlled by the controller 35, wherein the actuator 37 comprises a hand wheel with thread rod or a register mechanically coupled to optical components for executing actuation when actuated by hand.

Furthermore it is possible to control the actuator 37 by the controller 35, though not in dependence on the working distance w detected by the distance sensor 31, but in dependence on an actuating signal transmitted to the controller 35 by a user via an input device 43, such as an electrical switch or the like.

Figure 2:
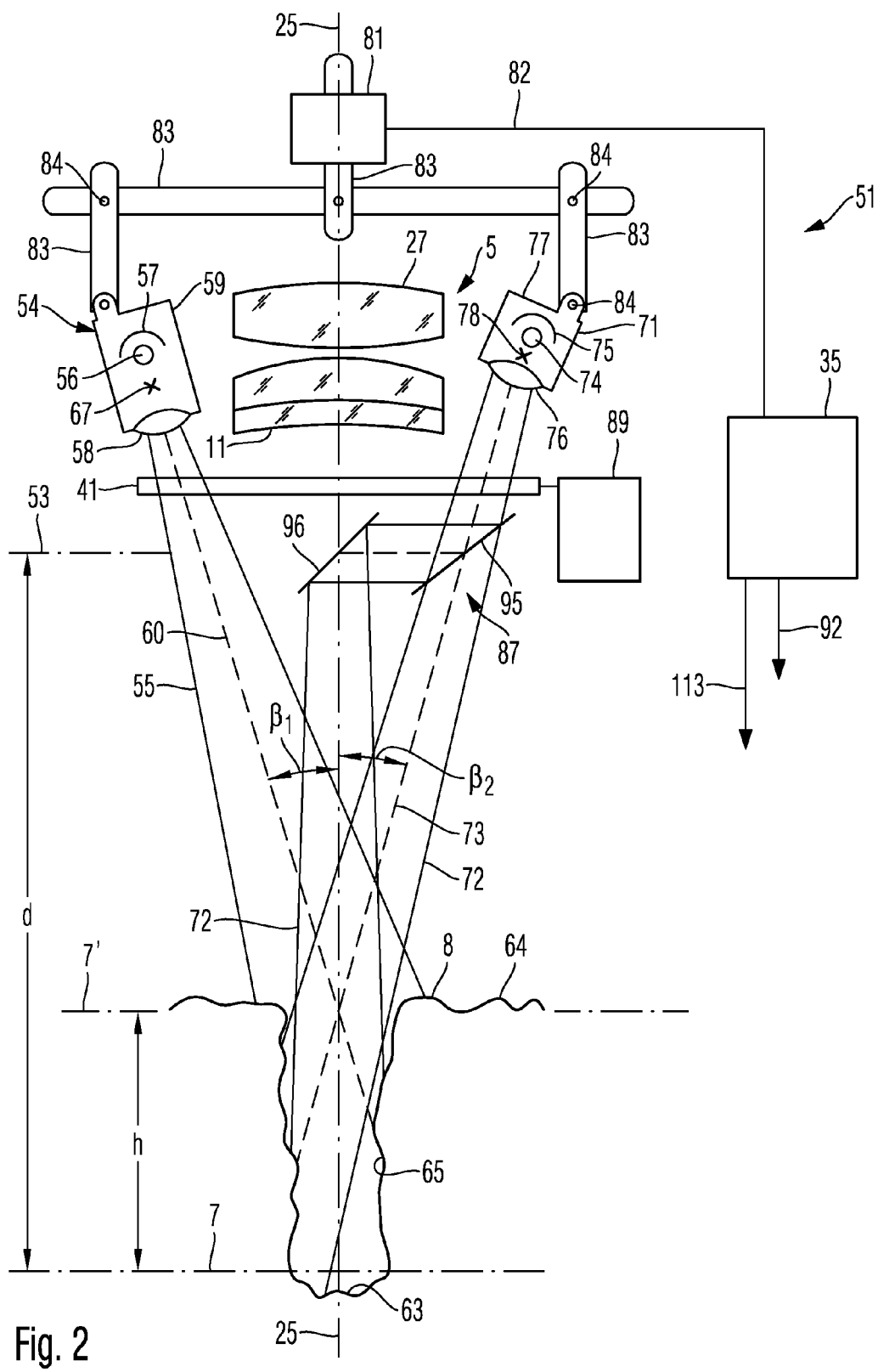
FIG. 2 is a schematic illustration showing other components of the stereo microscope system shown in FIG. 1.

A schematic illustration of an illumination system 51 of the microscopy system 1 is shown in FIG. 2. The zoom optics 15, 16 and the oculars 17, 18 are not shown in FIG. 2, and the illustration of FIG. 2 is a projection in a direction orthogonal to a direction selected for a projection of FIG. 1.

Figure 3:
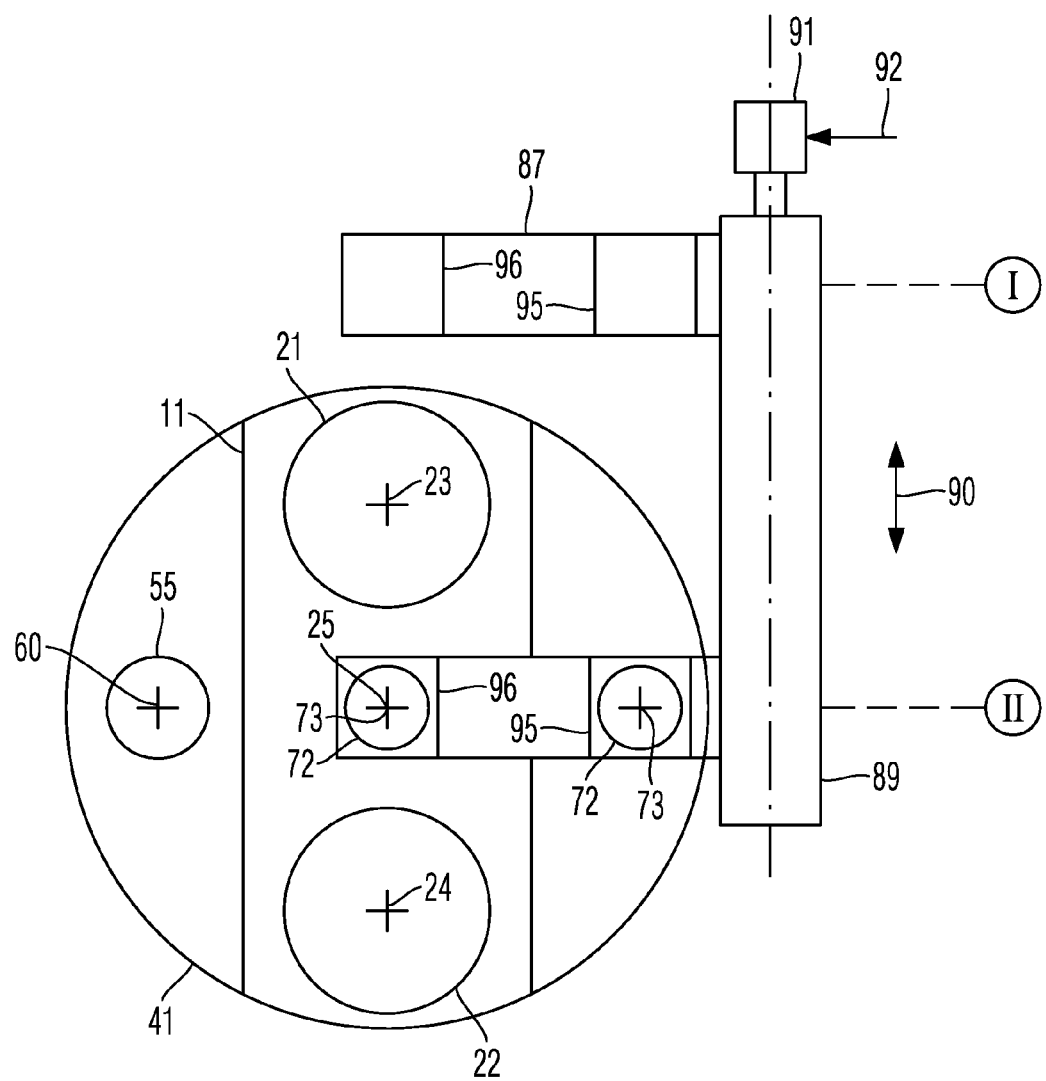
FIG. 3 is an elevational view of details of the stereo microscope system shown in FIGS. 1 and 2.

FIG. 3 is a plan view from below along the optical axis 25 onto a plane 53 which is disposed in front of the front plate 41 at a distance d from the object plane 7 and which is oriented orthogonally with respect to the optical axis 25.

It is obvious from FIG. 3 that the front plate 41 has a circular shaped cross section, while the lenses 11, 27 of the objective lens 5 have a reduced cross section, which is dimensioned such that the partial beam bundles 21 and 22 contributing to the generation of the imaging traverse the lenses 11, 27 without disturbance.

The illumination system 51 comprises a first illumination system 54 configured to generate a first illumination beam 55 directed towards the object plane 7. The first illumination system 54 is disposed adjacent to the objective lens 5 and comprises a light source 56, such as a Halogen lamp, a reflector 57 and a collimator lens 58 supported by a chassis 59 of the light source 54.

In the illustration of FIG. 2, a main axis 60 of the first illumination light beam 55 intersects the optical axis 25 in a plane 7' disposed at a distance h from the object plane 7 which is imaged sharply by the microscope optics 3. A situation in which a bottom 63 of a narrow body cavity 65 is to be observed by the stereo microscope system 1 is schematically shown in FIG. 2, wherein the bottom 63 of the body cavity 65 approximately coincides with the object plane 7 of the microscope optics 3, while a body surface 64 is disposed in a plane 7' at the distance h from the object plane 7. The section of the first illumination light beam 55 with the plane 7' is substantially bigger than an aperture cross section of the body cavity 55. However, the central axis 66 of the first illumination light beam 55 intersects the optical axis 25 in a proximity of the plane 7' and not in a proximity of the object plane 7 so as to allow a portion of the first illumination light beam 55 to enter the body cavity 65 through the aperture cross section of the body cavity 65, wherein the portion of the first illumination light beam 55 entering the body cavity 65 is as big as possible.

For allowing adjustment to body cavities of varying depths, the chassis 59 of the light source 54 is suspended so as to allow rotation around a rotating axis 67. By rotating the light source 54 about the rotating axis 67 it is possible to change an angle $\beta_1$, under which the central axis 60 of the beam 55 is oriented with respect to the optical axis 25. Thus, if the distance d-h of the plane 7' from the objective lens changes, the angle $\beta_1$ of the beam 55 relative to the optical axis 25 can be changed such that a major portion of the beam 55 still enters the body cavity through the orifice in plane 7'.

The illumination system 51 comprises a second illumination system 71 configured to generate a second illumination light beam 72 directed to the object plane 7, wherein a central axis 73 of the second illumination beam 72 intersects the plane 53 at a distance from the optical axis 25. The central axis 73 intersects the optical axis 25 of the objective lens 5 in a proximity of the plane 7'. Unlike the first illumination light beam 55, the second illumination light beam 72 has a smaller beam cross section and is intended to substantially completely enter the body cavity 65 via its aperture cross section for providing as much illumination light as possible at the bottom 63 of the body cavity 65.

Herein, the second illumination system 71 has a similar configuration as the first illumination system 54 and comprises, for example, a light source 74, a reflector 75 and a collimator lens 76 which are supported at a chassis 77, which can be rotated about an axis 78 for adjusting an angle $\beta_2$ between the central axis 73 and the optical axis 25.

There is provided a common actuator 81, such as a motor, configured to change the angles $\beta_1$ and $\beta_2$ of the illuminations systems 54 and 71, respectively, wherein the actuator 81 is controlled by a controller 35 via a control line 82. The controlled motion of the actuator 81 is mechanically transferred to the chassis 59 of the first illumination system 54 or to the chassis 77 of the second illumination system 71 via several rods 83 and joints 84 in order to cause rotation of the light sources 59 and 71 abound the axes 67 and 78, respectively.

Although the full cross section of the second illumination light beam 72 enters the aperture of the body cavity 65 in the condition shown in FIG. 2, the bottom 63 of the body cavity 65 is not optimally illuminated since the illumination light beam 72 is oriented under an angle $\beta_2$ relative to the axis 25, and shadows in which no illumination light or a reduced amount of illumination light is incident on the bottom 63 of the cavity remain.

In order to improve this situation, the illumination system 51 comprises a mirror assembly 87, which can be selectively positioned in the beam path of the second illumination light beam 72 generated by the second illumination system 71 and which is configured to deflect the second illumination light beam 72. In the elevational view of FIG. 3, the mirror assembly 87 is shown in two states, namely in a state denoted by I in which the mirror assembly 87 is completely removed from the beam paths of the microscope system, and in a state denoted by II in which the mirror assembly 87 is positioned in particular in the beam path of the second illumination light beam 72. Herein, the mirror assembly 87 can be displaced with respect to a support 89, as indicated by an arrow 90. This displacement may be caused by an actuator 91 which is controlled by a controller 35 via a control line 92.

The mirror assembly 87 comprises a first mirror 95 and a second mirror 96. When the mirror assembly 87 is positioned in the beam path of the second illumination light beam 72 in the state II, the plane 53 and the central axis 73 of the second illumination light beam 72 intersect the first mirror 95. The first mirror 95 is oriented to direct the second illumination light beam 72 towards the optical axis 25 and onto the second mirror 96 when the mirror assembly 87 is positioned in the state II. The second mirror 96 is oriented to deflect the second illumination light beam 72 towards the object plane 7, when the mirror assembly 87 is in the state II. As the second mirror 96 is disposed at a substantially smaller distance from the optical axis 25 than the first mirror 95, the central axis 73 of the second illumination light beam 72 and the optical axis 25 form a substantially smaller angle after reflection at the second mirror 96 as corresponding to the angle $\beta_2$ formed by the central axis 73 and the optical axis 25 in the state I, in which the mirror assembly 87 is not positioned in the beam path of the second illumination light beam 72. The second illumination light beam 72 and the optical axis 25 form a comparable small angle, when the second illumination beam 72 enters the body cavity 65 in the state II. Therefore, the second illumination light beam 72 may illuminate well the bottom 63 of the body cavity 65.

Figure 4:
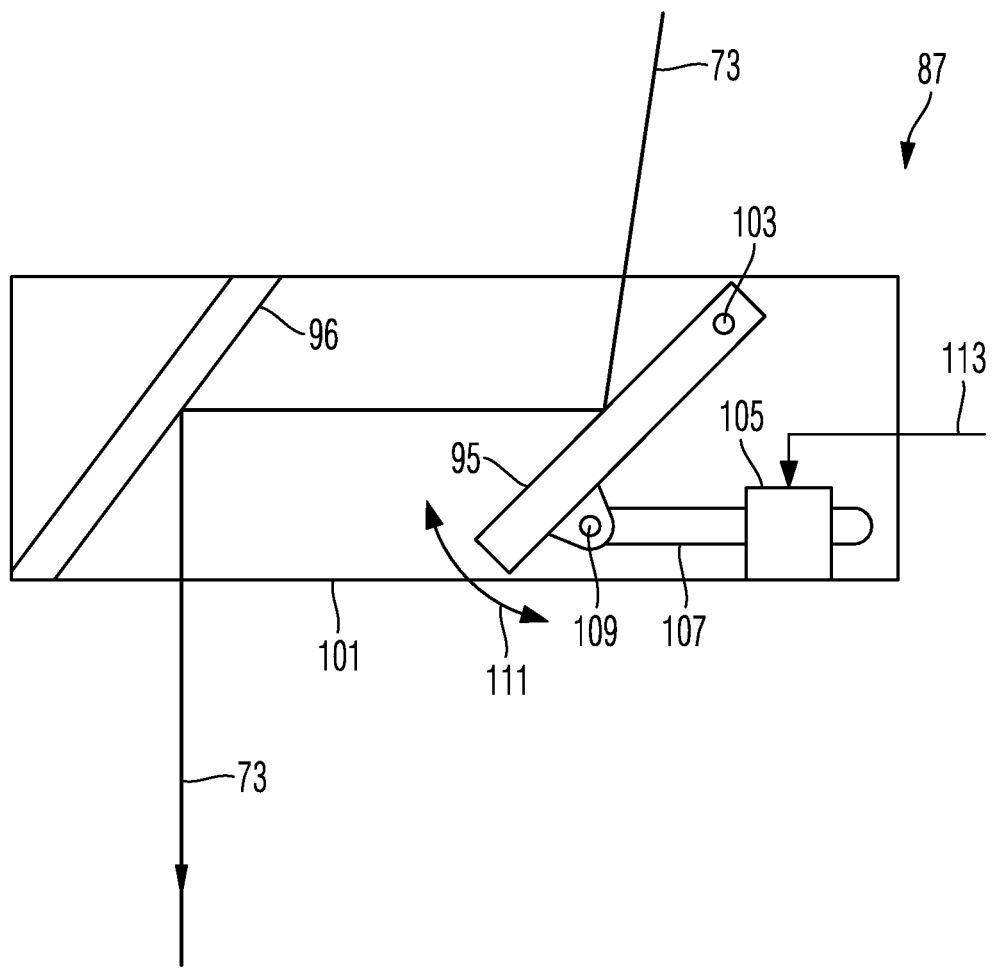
FIG. 4 is a more detailed illustration of a mirror assembly which can be used in the stereo microscope system shown in FIGS. 1 to 3.

FIG. 4 shows details of the mirror assembly 87 in sectional view. Herein, the second mirror 96 is fixed to the support 101, while the first mirror 95 is held rotatably with respect to a rotation axis 103 at the support 101. Furthermore, an actuator 105 is held at the support 101, the actuator 105 being configured to displace a rod 107 coupled to the first mirror 95 via a joint 109 for changing the rotating position of the first mirror 95 around the rotation axis 103, as indicated by an arrow 111 in FIG. 4. The actuator 105 is controlled by the controller 35 via a control line 113.

The actuator 105 is controlled by the controller 35 in dependence on an actuating position of the actuator 81 such that the changes caused in the angle $\beta_2$ by the actuator 81 are compensated such that the central axis 73 is essentially oriented in parallel to the optical axis 25 of the objective lens 5 after reflection at the second mirror 96, wherein the angle $\beta_2$ is formed by the central axis 73 and the optical axis 25 before impinging onto the first mirror 95. Therefore, there is always a good illumination of the bottom 63 of the body cavity 65 assured, when the mirror assembly 87 is positioned in the beam path of the second illumination light beam 72 in the state II, even though the central axis 60 of the first illumination light beam 55 intersects the optical axis 25 in the region around the plane 7' which is disposed at the distance h from the object plane 7.

In the above described embodiment, the mirrors 95 and 96 have plane mirror faces. However, it is also possible to provide the second mirror 96 or the first mirror 95 or both mirrors 96 and 95 with curved mirror faces, such as a convex mirror face or a concave mirror face, for modifying a divergence of the illumination light beam 72.

In the above described embodiment, the angle $\beta_1$ or $\beta_2$ formed by the central axis 60 or 73 of the illumination light beams 55 and 72, respectively, and the optical axis 25 are adjusted by the common actuator 81 which is mechanically coupled to both illumination systems 54 and 71, respectively. However, it is also possible to adjust both angles $\beta_1$ and $\beta_2$ by two separate actuators, each actuator being controlled separately and independently of the other actuator by the controller 35. Furthermore it is possible to mechanically couple other actuating functions of the stereo microscope system 1 to each other and to generate an actuating motion by a common actuator. Thus, the actuator 105 configured to adjust the rotating position of the first mirror 95, for example, may be mechanically coupled to the actuator configured to adjust the rotating position of the second illumination system 71 and/or to configured to adjust the rotating position illumination system 54 so as to control the actuating motions by a single motor-driven means of the controller 35.

It is also possible to couple one of the actuators 81 configured to adjust the rotating position of the illumination systems 71 and 54 or the actuator 51 configured to adjust the rotating position of the first mirror 95 to the actuator 35 configured to adjust the working distance w so as to allow the controller 35 to cause the corresponding actuating functions by means of a common motor-driven actuator.

According to an embodiment, the invention provides an illumination system of the microscopy system comprising an actuator configured to change an angle of an illumination light beam and a mirror assembly which can be selectively positioned in the beam path of the illumination light beam. The mirror assembly may comprise an actuator configured to change an orientation of a mirror with respect to another mirror.

While the present invention has been shown and described herein in what is believed to be the most practical and preferred embodiments, it is recognized that many alternatives, modifications, and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A stereo microscope system comprising: microscope optics configured to image an object, the microscope optics having an object plane and including an objective lens having an optical axis, the microscope optics being further configured to provide two partial beam bundles to the user; an illumination system configured to direct a first illumination light beam towards the object plane, wherein a central axis of the first illumination light beam intersects a plane which is oriented orthogonally with respect to the optical axis at a distance from the optical axis, and wherein the illumination system comprises a first actuator for changing an angle between the central axis of the first illumination light beam and the optical axis at the plane; wherein the illumination system comprises a mirror assembly and a second actuator configured to selectively transferring the mirror assembly from a first state in which the mirror assembly is positioned in a beam path of the first illumination light beam, to a second state in which the mirror assembly is removed from the beam path; wherein the mirror assembly comprises a first mirror and a second mirror, wherein the plane intersects the first mirror when it is in the first state, wherein the first mirror, when it is in the first state, is positioned to be intersected by the central axis of the first illumination light beam, and wherein the first mirror, when it is in the first state, is oriented to direct the first illumination light beam onto the second mirror, wherein the second mirror, when it is in the first state, is positioned at a second plane and oriented to deflect the first illumination light beam towards the object plane, and wherein the second mirror is positioned at a smaller distance from the optical axis than the first mirror, wherein the first illumination light beam is adjacent to, and not overlapping the two partial beam bundles at the plane, and wherein the deflected first illumination light beam is adjacent to, and not overlapping the two partial beam bundles at the second plane.

2. The stereo microscope system according to claim 1 further comprising a third actuator configured to change an orientation of at least one of the first mirror and the second mirror with respect to the central axis of the first illumination light beam.

3. The stereo microscope system according to claim 2 further comprising a controller configured to control the third actuator in dependence on an actuating position of the second actuator.

4. The stereo microscope system according to claim 2 wherein the third actuator comprises a motor.

5. The stereo microscope system according to claim 1 further comprising a fifth actuator configured to displace lens elements of the objective lens relative to each other for changing a distance between the object plane and the objective lens.

6. The stereo microscope system according to claim 5 wherein the fifth actuator comprises a motor.

7. The stereo microscope system according to claim 1 wherein the illumination system is configured to direct a second illumination light beam towards the object plane.

8. The stereo microscope system according to claim 7 wherein the illumination system comprises a fourth actuator configured to change an angle between a central axis of the second illumination light beam and the optical axis.

9. The stereo microscope system according to claim 8 wherein the fourth actuator comprises a motor.

10. The stereo microscope system according to claim 1 further comprising a distance sensor configured to detect a distance between the object and the microscope optics.

11. The stereo microscope system according to claim 1 wherein at least one of the first actuator and the second actuator comprise a motor.

12. The stereo microscope system according to claim 1 wherein at least one of the first mirror and the second mirror has a planar reflective surface.

13. A stereo microscope system comprising:
microscope optics configured to image an object, the microscope optics having an object plane and including an objective lens having an optical axis;
an illumination system configured to direct a first illumination light beam towards the object plane, wherein a central axis of the first illumination light beam intersects a plane which is oriented orthogonally with respect to the optical axis at a distance from the optical axis, and wherein the illumination system comprises a first actuator for changing an angle between the central axis of the first illumination light beam and the optical axis at the plane;
wherein the illumination system comprises a mirror assembly and a second actuator configured to selectively transferring the mirror assembly from a first state in which the mirror assembly is positioned in a beam path of the first illumination light beam, to a second state in which the mirror assembly is removed from the beam path;
wherein the mirror assembly comprises a first mirror and a second mirror, wherein the plane intersects the first mirror when it is in the first state, wherein the first mirror, when it is in the first state, is positioned to be intersected by the central axis of the first illumination light beam, and wherein the first mirror, when it is in the first state, is oriented to direct the illumination light beam onto the second mirror, wherein the second mirror, when it is in the first state, is oriented to deflect the first illumination light beam towards the object plane, and wherein the second mirror is positioned at a smaller distance from the optical axis than the first mirror,
wherein the illumination system comprises a fourth actuator configured to change an angle between a central axis of a second illumination light beam and the optical axis, further comprising a link between a third actuator and the fourth actuator configured such that actuating movements of the third and fourth actuators occur simultaneously.

14. The stereo microscope system according to claim 13, wherein the fourth actuator comprises a motor.

15. The stereo microscope system according to claim 13, wherein the illumination system is configured to direct the second illumination light beam towards the object plane.

16. The stereo microscope system according to claim 13, wherein at least one of the first actuator and the second actuator comprise a motor.

17. The stereo microscope system according to claim 13, wherein at least one of the first mirror and the second mirror has a planar reflective surface.

18. A stereo microscope system comprising:
microscope optics configured to image an object, the microscope optics having an object plane and including an objective lens having an optical axis;
an illumination system configured to direct a first illumination light beam towards the object plane, wherein a central axis of the first illumination light beam intersects a plane which is oriented orthogonally with respect to the optical axis at a distance from the optical axis, and wherein the illumination system comprises a first actuator for changing an angle between the central axis of the first illumination light beam and the optical axis at the plane;

wherein the illumination system comprises a mirror assembly and a second actuator configured to selectively transferring the mirror assembly from a first state in which the mirror assembly is positioned in a beam path of the first illumination light beam, to a second state in which the mirror assembly is removed from the beam path;

wherein the mirror assembly comprises a first mirror and a second mirror, wherein the plane intersects the first mirror when it is in the first state, wherein the first mirror, when it is in the first state, is positioned to be intersected by the central axis of the first illumination light beam, and wherein the first mirror, when it is in the first state, is oriented to direct the illumination light beam onto the second mirror, wherein the second mirror, when it is in the first state, is oriented to deflect the first illumination light beam towards the object plane, and wherein the second mirror is positioned at a smaller distance from the optical axis than the first mirror, further comprising a distance sensor configured to detect a distance between the object and the microscope optics, further comprising a fifth actuator configured to displace lens elements of the objective lens relative to each other for changing a distance between the object plane and the objective lens, and a controller configured to control the second actuator in dependence on at least one of an actuating position of the fifth actuator and a detection signal of the distance detector.

19. The stereo microscope system according to claim 18, wherein at least one of the first actuator and the second actuator comprise a motor.

20. The stereo microscope system according to claim 18, wherein at least one of the first mirror and the second mirror has a planar reflective surface.

21. The stereo microscope system according to claim 18, wherein the illumination system is configured to direct a second illumination light beam towards the object plane.

* * * * *